(12) United States Patent
Richard

(10) Patent No.: US 7,836,891 B2
(45) Date of Patent: Nov. 23, 2010

(54) REVERSIBLE ORTHOSIS

(75) Inventor: Dominique Richard, Aurec/Loire (FR)

(73) Assignee: Richard Freres SA (FR)

( * ) Notice: Subject to any disclaimer, the term of this patent is extended or adjusted under 35 U.S.C. 154(b) by 472 days.

(21) Appl. No.: 11/353,570

(22) Filed: Feb. 14, 2006

(65) Prior Publication Data
US 2006/0289018 A1    Dec. 28, 2006

(30) Foreign Application Priority Data
Feb. 15, 2005    (FR) .................................. 05 01507

(51) Int. Cl.
*A61F 5/00*    (2006.01)
*A61F 5/37*    (2006.01)
*A41D 1/04*    (2006.01)
(52) U.S. Cl. ....................... 128/878; 128/869; 128/874; 602/4; 2/462
(58) Field of Classification Search ................. 128/846, 128/869, 870, 874, 876, 878, 881; 602/4, 602/5, 20, 60, 62, 75, 78, 79; 2/459–462, 2/44, 45
See application file for complete search history.

(56) References Cited

U.S. PATENT DOCUMENTS 3,297,026 A * 1/1967 Pelt .............................. 128/878
4,550,724 A * 11/1985 Berrehail ..................... 128/874
5,289,619 A *  3/1994 Pileggi ......................... 24/306

* cited by examiner

*Primary Examiner*—Patricia M Bianco
*Assistant Examiner*—Keri J Nicholson
(74) *Attorney, Agent, or Firm*—Cantor Colburn LLP

(57) ABSTRACT

This orthopedic orthosis, includes a textile article with first and second faces; the orthosis can be fitted in place such that either the first and second faces can equally well contact a patient limb. The orthosis has at least one fastening tab including an active face with fastening elements that may cooperate with first or second securing means arranged respectively on the first the second faces of the textile article, and an inactive face opposite the active face, said fastening tab being fixed non-removably via its inactive face on a zone contiguous to an edge of the textile article, so as to be able to pivot about an axis substantially parallel to this edge, between a first position, in which the active face catches by contact on the first securing means, and a second position, in which the active face catches by contact on the second securing means.

10 Claims, 4 Drawing Sheets

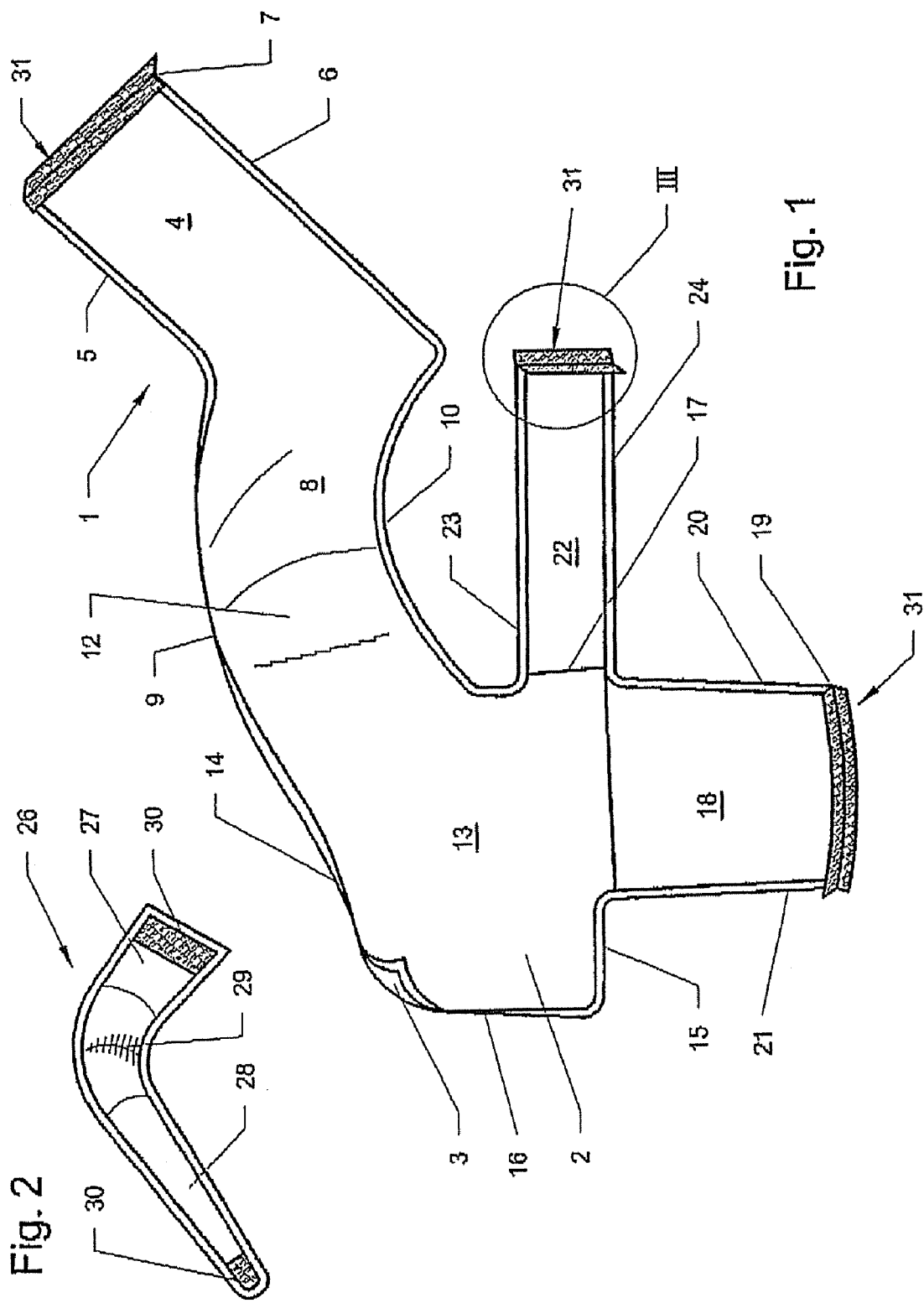

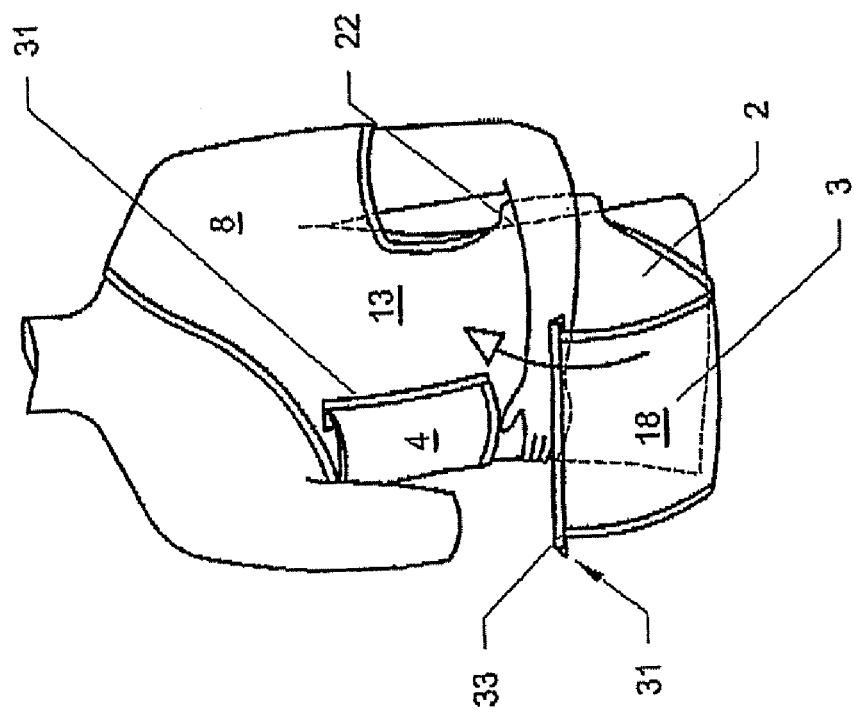
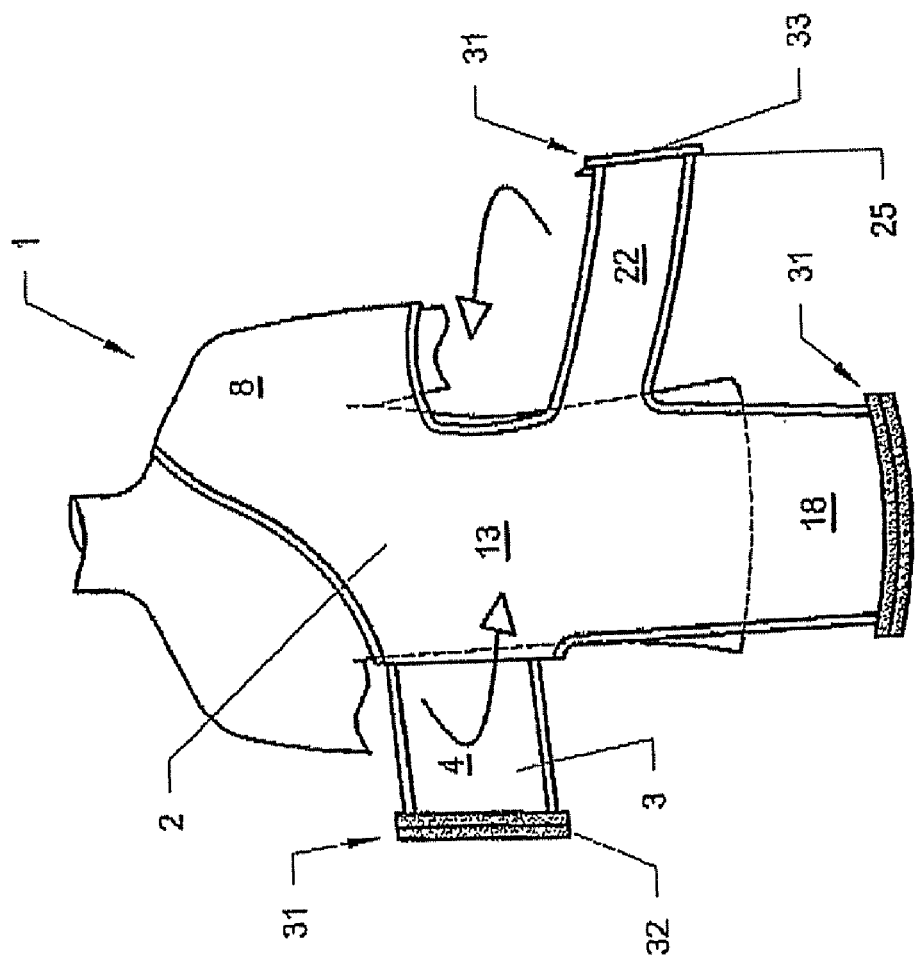

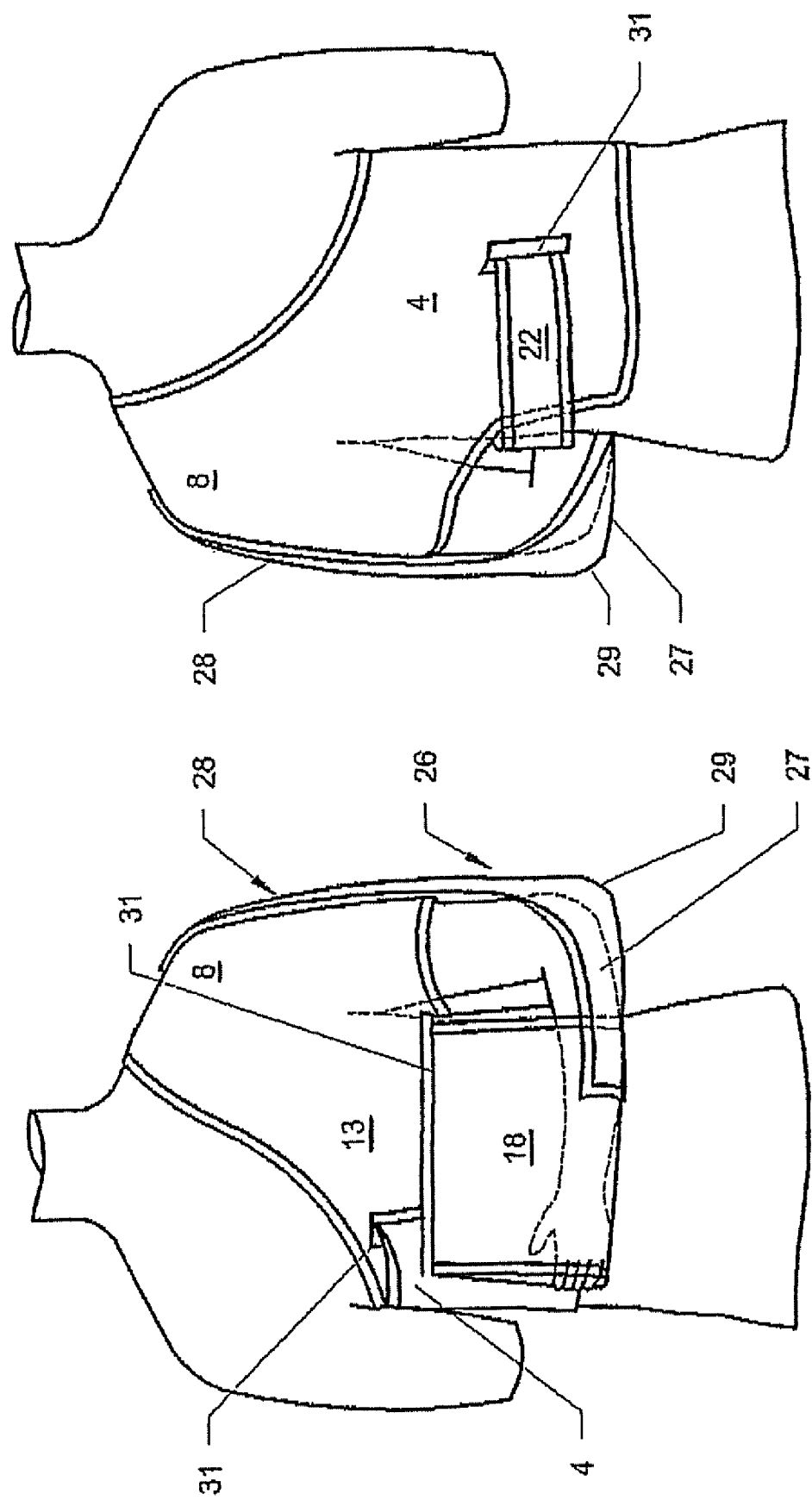

REVERSIBLE ORTHOSIS

BACKGROUND OF THE INVENTION

The present invention relates to a reversible orthosis, of the type comprising a textile article which has opposite first and second faces and which is intended to be fitted around a part of the body of a user in order to support and/or immobilize this part of the body.

DESCRIPTION OF THE PRIOR ART

The reversibility of an orthosis can be made possible in particular by its not having a wrong side and thus being able to be worn either with its first face or second face in contact with a user's body. Thus, a reversible orthosis can be used equally well either for a left part or right part of the user's body.

The invention relates in particular to an orthopedic vest for supporting and immobilizing the shoulder, but can be used for other orthoses, for example for wrist orthoses.

Reversible orthopedic vests are already known which are placed around a user's thorax, shoulder and arm and are held in position by fastening systems with loops and hooks of the Velcro® type.

A vest of this kind is described, for example, in document U.S. Pat. No. 4,550,724. So that this vest can be effectively be reversible, it is necessary to provide each of the faces of the textile article with adhesive bands. This increases the cost of the vest, but it also poses another problem. Namely, when the vest is fitted on a user, one pair of bands with loops and hooks is not used, the unused pair depending on which shoulder, left or right, is fitted. This has the result that the first of the bands not used can be in contact with the user's skin, which detracts from the comfort experienced by the user, and, on the other hand, the second unused band is exposed on the outside of the vest and can for this reason catch on different objects or materials.

To overcome this disadvantage, it is possible to provide a flap that is equipped with a band complementing the unused band and intended to cooperate with it. This solution therefore requires an additional element, which poses a number of disadvantages. First, the increased quantity of textile and of textile bands of the Velcro® type used leads to an increase in the cost of the vest. Moreover, the flap stiffens the vest and, for this reason, the latter proves less effective and less comfortable because it is more difficult to adapt to the user's anatomy. Finally, the additional thickness created detracts from the esthetic quality of the vest.

SUMMARY OF THE INVENTION

The object of the present invention is to overcome the disadvantages mentioned above.

To this end, the invention relates to an orthopedic orthosis which can support and/or immobilize at least one limb of a patient, comprising a textile article with first and second faces, either of which first and second faces can equally well come into contact with the limb or limbs of the patient.

The orthosis is more particularly characterized in that it additionally has at least one fastening tab comprising an active face with fastening elements that are able to cooperate with first or second securing means arranged respectively on the first face and the second face of the textile article, and an inactive face opposite the active face, said fastening tab being fixed non-removably via its inactive face on a zone of the textile article contiguous to one of the edges of said textile article, so as to be able to pivot, about a pivot axis substantially parallel to this edge, between a first position, in which the active face catches by contact on the first securing means, and a second position, in which the active face catches by contact on the second securing means.

In this way, the active face of the tab can be oriented in the required manner, in order to be placed opposite the surface on which it is to be fastened. Thus, the orthosis is completely adaptable to the left or right half of the human body by virtue of its shape and the reversibility of the textile article, but also by virtue of the ability of the fastening means to pivot. The tab forms a kind of continuation of the first face or second face depending on the direction of use of the textile article.

The tab can comprise substantially identical first and second wings extending on either side of the pivot axis, the first wing being able to be folded back against the first face of the textile article, in the first position of the tab, and the second wing being able to be folded back against the second face of the textile article, in the second position of the tab.

The entire active surface of the tab is used irrespective of the direction in which the textile article is arranged, that is to say irrespective of the orientation of the tab.

According to a first embodiment, the tab is fixed on a band of the textile article delimited on one side by the edge of the textile article and on the other side by the pivot axis of the tab. This method of fixing is particularly robust.

According to a second embodiment, the tab is fixed substantially on the edge of the textile article, said edge forming the pivot axis of the tab. This results in a perfectly symmetrical structure, without excess thickness, and in easy pivoting of the tab.

The tab can be fixed on the textile article by sewing, welding or bonding.

According to one possible embodiment, the tab extends along substantially the entire length of the edge of the textile article. Alternatively, it would be possible to provide several bands spaced apart from one another along the edge.

For example, the fastening elements are formed by hooks, and the first and second securing means arranged respectively on the first face and second face of the textile article are formed by loops, establishing a self-adhering fixation system of the Velcro® type. This arrangement proves particularly comfortable for the patient since he then has a textile with loops arranged against his skin, which has a pleasant and gentle feel.

The first and/or second securing means comprise a band attached to the textile article or are formed by the actual textile of the textile article; this arrangement proves extremely practical because it does not result in additional thickness.

According to one possible embodiment, the textile article is intended to form an orthopedic vest for supporting and immobilizing the shoulder, and comprises:

a first panel intended to cover the rear area of the user's thorax;

a second panel forming a lateral continuation of the first panel and intended to cover the front area and rear area of the shoulder and of the arm;

a third panel forming a lateral continuation of the second panel, remote from the first panel, and intended to cover the front area of the thorax;

a fourth panel forming a continuation of a portion of the lower part of the third panel and intended to serve as a rest for the forearm.

At least one fastening tab can be fixed near the edge of the first panel remote from the second panel and/or the edge of the fourth panel remote from the third panel, said tab being intended to cooperate with securing means formed on the third panel.

The orthosis can additionally comprise a belt extending laterally from the lower part of the third panel in the same direction as the second panel, and a fastening tab fixed near the edge of the belt remote from the third panel, said tab being intended to cooperate with securing means formed on the first panel.

BRIEF DESCRIPTION OF THE FIGURES

To ensure that it is clearly understood, the invention is described in further detail below with reference to the attached figures which depict, by way of non-limiting examples, several possible embodiments of orthoses according to the invention.

FIG. 1 is a plan view of a textile article intended to form an orthopedic vest, a corner of the textile article having been curved back for clearer illustration;

FIG. 2 is a perspective view of a strap intended to be joined to the textile article from FIG. 1;

FIGS. 7 and 8 show the steps involved in fitting the vest from FIG. 1 in place; and FIGS. 9 and 10 are schematic representations showing a user fitted with the vest from FIG. 1, seen from the front and from the back, respectively.

DESCRIPTION OF THE INVENTION

Figure 5:
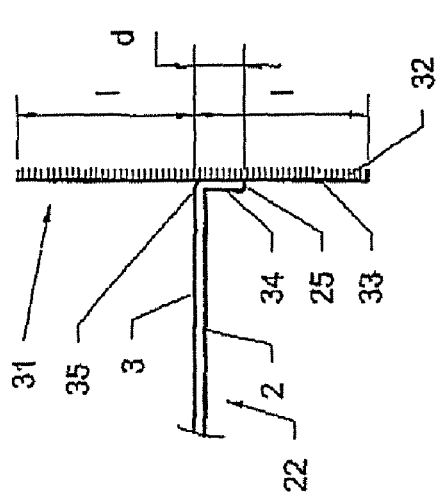
FIGS. 5 and 6 are schematic representations of the join between the tab and the textile article, according to the first embodiment and second embodiment, respectively.

FIG. 1 shows a textile article 1, in a plan view, which will form an orthopedic vest when fitted in place on a user.

The textile article 1 is generally flat and has a first face 2 and an opposite second face 3, the latter being partially visible in the corner shown partially folded back for this purpose.

The textile article 1 in the first instance comprises a substantially rectangular first panel 4 intended to cover the rear area of a user's thorax and delimited in particular by an upper edge 5, a lower edge 6 and a free edge 7.

The textile article 1 also comprises a second panel 8 forming a lateral continuation of the first panel 4 remote from the free edge 7 and intended to cover the front area and rear area of the shoulder and of the arm. The second panel 8 forms an inwardly curved bend at its lower part and is delimited in particular by a curved upper edge 9 and a curved lower edge 10. In addition, a curved line 11 extending between the upper edge 9 and lower edge 10, substantially at the center of the second panel 8, forms a hump 12 located in the upper part of the second panel 8, substantially centered laterally. In FIG. 1, the hump 12 protrudes upward relative to the general plane of the textile article 1. The concavity of the hump 12 can be inverted such that the hump 12 can protrude downward relative to the general plane of the textile article 1. It is particularly by virtue of this inversion of the concavity that the vest can be adapted to the left or right shoulder of a user.

A third and substantially rectangular panel 13 forms a lateral continuation of the second panel 8 remote from the first panel 4 and is intended to cover the front area of the user's thorax. The third panel 13 is delimited in particular by an upper edge 14, a lower edge 15 and a free edge 16. The distance between the upper edge 14 and the lower edge 15 of the third panel 13 is greater than the distance between the upper edge 9 and lower edge 10 of the second panel 8. The third panel 13 thus comprises a lateral edge 17, of small height, opposite the free edge 16 and not joined to the second panel 8.

A fourth panel 18 continues a portion of the third panel 13 at the latter's lower part and is intended to serve as a rest for the user's forearm. The fourth panel 18 has the general shape of a trapezoid whose bases form the upper edge 19 and lower (free) edge 18, the upper edge being coincident with the lower edge 15 of the third panel 13. The fourth panel 18 is additionally delimited by a lateral edge 20 situated substantially in a continuation of the lateral edge 17 of the third panel 13, and a lateral edge 21. The distance between the lateral edges 20, 21 of the fourth panel 18 is less (for example of the order of two thirds) than the distance between the free edge 16 and lateral edge 17 of the third panel 13.

Finally, the textile article 1 comprises a belt 22 extending laterally from the edge 17 of the third panel 13 toward and substantially as far as the first panel 4, substantially parallel to the lower edge 15 of the third panel 13. The belt has an upper edge 23 and a lower edge 24 and also a free edge 25 remote from the lateral edge 17.

The first and second faces 2, 3 are made of a material having loops, in the manner of the loops in a fastener of the Velcro® type. For example, the textile article 1 can be made of polyurethane foam covered with a "down" or duvetine of polyamide loops. Alternatively, the first and second faces 2, 3 could be without loops and, instead, could be provided with affixed tapes which themselves would have loops.

FIG. 2 shows a strap 26 comprising a first rectangular panel 27 and a second substantially rectangular panel 28 tapered to a point, these panels being joined by a curved transverse line 29 which gives the strap an elbow shape. At its ends, and on the same side, the first panel 27 has two zones 30 provided with fastening elements in the manner of hooks of a Velcro® system.

In a manner specific to the invention, the free edge 7 of the first panel 4, the free edge 19 of the fourth panel 18, and the free edge 25 of the belt 22 of the textile article 1 each comprise a fastening tab 31 extending along the entire length of said edge. The fastening tab 31 joined to the belt 22 will now be described in more detail with reference to FIGS. 3 to 6, it being understood that the other tabs and their method of fixing are similar.

The tab 31 is a flat rectangle and has an active face 32 comprising fastening elements of the hook type as in a Velcro® system. The opposite face, called the inactive face 33, has no such fastening elements. The tab 31 is fixed via its inactive face 33 to the textile article 1, in this case the belt 22, near the edge in question, in this case the free edge 25.

Figure 3:
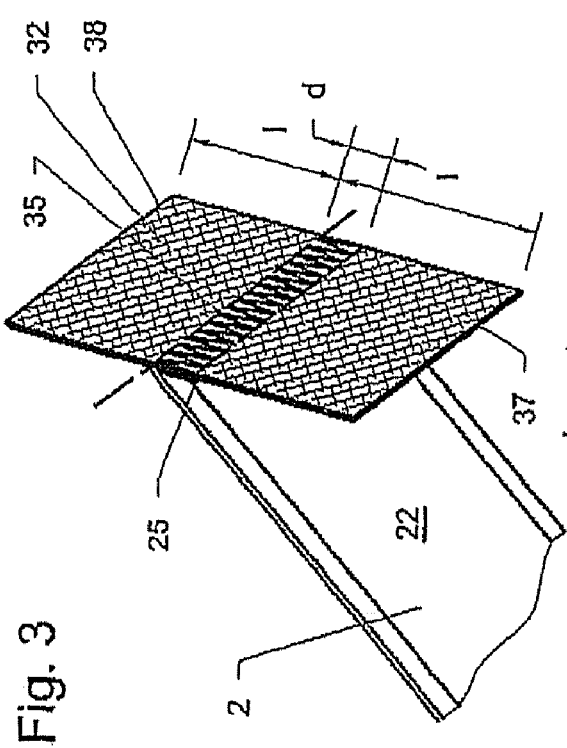
FIG. 3 is an enlarged view of the detail III from FIG. 1, showing the fastening tab according to a first embodiment.
Figure 4:
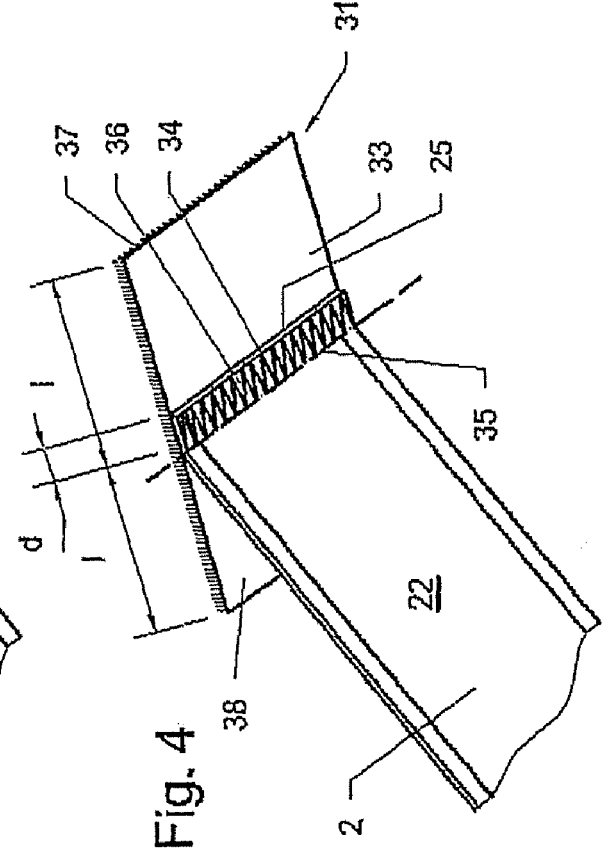
FIG. 4 is a view similar to FIG. 3, the fastening tab having pivoted relative to its pivot axis.

According to a first embodiment, shown in FIGS. 3 to 5, the tab 31 is fixed to a band 34 of the belt 22, of width d, limited on the one hand by the edge 25 and on the other hand by a line 35 parallel to the edge 25. The fixation is in this case effected by a seam 36 of zigzag configuration. A straight seam could also be used.

The band 34 is not fixed to the tab 31 in a centered position, but instead in such a way that the line 35 is situated substantially at the center of the tab 31 and thus defines two wings 37, 38 of equal length 1. By virtue of the flexibility of the textile article 1 and of the arrangement of the seam 36, the tab 31 is able to pivot about the line 35, as is shown in FIGS. 3 and 4. In a first extreme position, the tab 31 is arranged in such a way that the inactive face 33 of the first wing 37 is folded back against the first face 2 of the textile article 1, and, in a second extreme position, the tab 31 is arranged in such a way that the inactive face 33 of its second wing 38 is folded back against the second face 3 of the textile article 1.

Thus, all of this is arranged as if the fastening elements of the active face 32 could be displaced from the first face 2 to the second face 3 of the textile article 1 depending on requirements, that is to say depending on whether one wishes to secure the first face or second face of the textile article 1, and this simply by pivoting the tab 31. It is therefore not necessary to provide fastening means on each of the faces 2, 3 of the textile article. In addition, when the tab 31 is in the first extreme position, the second face 3 of the textile article 1 is without any fastening means (and vice versa in the second extreme position), and this avoids the risks of accidental fastening.

Figure 6:
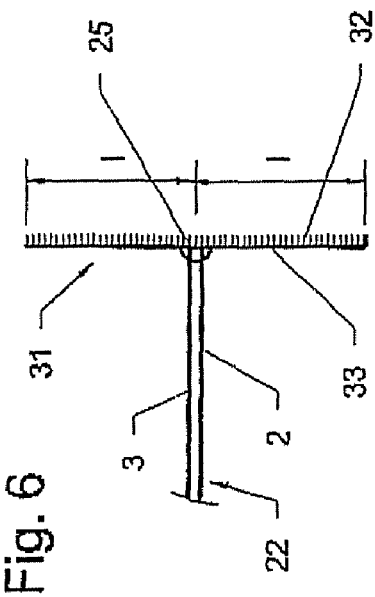

According to a second embodiment shown in FIG. 6, the tab 31 is fixed to the edge 25 of the belt 22 by button points. In this case, the edge 25 is situated at the center of the tab 31, thereby defining two wings 37, 38 of equal width 1, and the tab 31 is able to pivot about the edge 25.

The tab 31 can be fixed to a zone of the textile article 1 comprising loops, either in a flat position, the totality of the active surface 32 being in contact with the same face of the textile article 1, or in an astride position, the active faces 32 of the two wings 37, 38 being folded back toward one another and enclosing between them the textile article 1.

The way in which the textile article is fitted in place on a user will now be described.

In a first step, the concavity of the hump 12 is oriented in the direction suitable for the injured shoulder that is to be immobilized. In the figures, the shoulder in question is the left shoulder, and the hump 12 has to be oriented as shown in FIG. 1. The face of the textile article 1 which will be oriented toward the user (the inside of the vest) is then the second face 3.

In a second step, the hump 12 is placed on the shoulder, the third panel 13 covering the front of the thorax, the fourth panel 18 descending over the thighs, and the first panel 4 covering the back (FIG. 7). The first panel 4 is wound around the user and folded back against the third panel 13 on which it is fixed, by cooperation between the hooks of the tab 31 and the loops of the textile of the third panel 13. For this purpose, the tab 31 is oriented such that its active face 32 is opposite the third panel 13.

Similarly, the belt 22 is wound around the user's waist and fastened, at the back, to the first panel 4.

The user then places the arm corresponding to the injured shoulder against his chest, then the fourth panel 18 is folded back toward the third panel 13, surrounding the arm (FIG. 8), and fastened via the tab 31 to the third panel 13.

The user can then fix the strap 26 around his elbow, said strap 26 being fixed, via the zones 30, under the fourth panel 18, beneath the forearm, and also on the second panel 8, on the shoulder.

To fit the same textile article 1 in place on the other shoulder, it suffices first to invert the concavity of the hump 12, then to place the textile article symmetrically to what has been described above (the second face 3 then being oriented outward from the vest and partially exposed) and to modify the orientation of the fastening tabs 31 simply by pivoting them about their pivot axis.

Thus, the invention affords a decisive improvement to the prior art by providing a reversible orthosis whose fastening means are themselves reversible.

It goes without saying that the invention is not limited to the embodiment described above by way of example, and instead it encompasses all the alternative embodiments.

The invention could therefore be employed for orthoses other than shoulder orthoses (for the wrists in particular).

The invention claimed is:

1. An orthopedic orthosis which can support and/or immobilize at least one limb of a patient, comprising a textile article with first and second faces, either of which first and second faces can equally well come into contact with the limb or limbs of the patient, wherein the orthosis additionally has at least one fastening tab configured to associate with the textile article, the fastening tab comprising an active face with fastening elements that are able to cooperate with first or second securing means arranged respectively on the first face and the second face of the textile article, and an inactive face opposite the active face, said fastening tab being fixed non-removably via its inactive face on a zone of the textile article contiguous to one of the edges of said textile article, so as to be able to pivot, about a pivot axis substantially parallel to this edge,
wherein the fastening tab comprises substantially identical first and second wings extending on either side of the pivot axis, the first wing being able to be folded back against the first face of the textile article, in the first position of the tab, and the second wing being able to be folded back against the second face of the textile article, in the second position of the tab, the active face of the first wing and the active face of the second wing being both configured to catch by contact one of the first or second securing means of the article when the tab is in either the first position or the second position,
wherein the textile article is intended to form an orthopedic vest for supporting and immobilizing the shoulder, and comprises:
a first panel intended to cover the rear area of the user's thorax;
a second panel forming a lateral continuation of the first panel and intended to cover the front area and rear area of the shoulder and of the arm;
a third panel forming a lateral continuation of the second panel, remote from the first panel, and intended to cover the front area of the thorax;
a fourth panel forming a continuation of a portion of the lower part of the third panel and intended to serve as a rest for the forearm.

2. The orthosis as claimed in claim 1, wherein the tab is fixed on a band of the textile article delimited on one side by the edge of the textile article and on the other side by the pivot axis of the tab.

3. The orthosis as claimed in claim 1, wherein the tab is fixed substantially on the edge of the textile article, said edge forming the pivot axis of the tab.

4. The orthosis as claimed in claim 1, wherein the tab is fixed on the textile article by sewing, welding or bonding.

5. The orthosis as claimed in claim 1, wherein the tab extends along substantially the entire length of the edge of the textile article.

6. The orthosis as claimed in claim 1, wherein the fastening elements are formed by hooks, and the first and second securing means arranged respectively on the first face and second face of the textile article are formed by loops, establishing a self-adhering fixation system of the hook and loop fastener type.

7. The orthosis as claimed in claim 1, wherein the first and/or second securing means comprise a band attached to the textile article.

8. The orthosis as claimed in claim 1, wherein the first and/or second securing means are formed within the actual textile of the textile article.

9. The orthosis as claimed in claim 1, wherein said orthosis comprises at least one fastening tab fixed near the edge of the first panel remote from the second panel and/or the edge of the fourth panel remote from the third panel, said tab being intended to cooperate with securing means formed on the third panel.

10. The orthosis as claimed in claim 1, wherein said orthosis additionally comprises a belt extending laterally from the lower part of the third panel in the same direction as the second panel, and a fastening tab fixed near the edge of the belt.

* * * * *